United States Patent [19]

Chapman et al.

[11] Patent Number: 5,976,884
[45] Date of Patent: Nov. 2, 1999

[54] METHODS FOR QUANTIFYING PHOTOREACTIONS IN LIGHT ACTIVATED MATERIALS

[75] Inventors: John R. Chapman, Lake Villa, Ill.; Jean M Mathias, Lillois, Belgium

[73] Assignee: Baxter International Inc., Deerfield, Ill.

[21] Appl. No.: 09/222,518

[22] Filed: Dec. 29, 1998

Related U.S. Application Data

[62] Division of application No. 08/771,206, Dec. 20, 1996, Pat. No. 5,866,074.

[51] Int. Cl.⁶ ................................................. G01N 21/78
[52] U.S. Cl. ........................... 436/34; 436/164; 436/904; 436/905
[58] Field of Search ............................ 436/34, 1, 2, 164, 436/904, 905

[56] References Cited

U.S. PATENT DOCUMENTS

| | | |
|---|---|---|
| 5,168,047 | 12/1992 | Kondo et al. . |
| 5,232,844 | 8/1993 | Horowitz et al. . |
| 5,290,221 | 3/1994 | Wolf, Jr. et al. . |
| 5,300,019 | 4/1994 | Bischof et al. . |
| 5,360,734 | 11/1994 | Chapman et al. . |
| 5,576,013 | 11/1996 | Williams et al. . |
| 5,597,722 | 1/1997 | Chapman et al. . |

*Primary Examiner*—Jeffrey Snay
*Attorney, Agent, or Firm*—Daniel D. Ryan; Denise M. Serewicz; Bradford R. L. Price

[57] ABSTRACT

Systems and methods treat biological fluids carrying contaminants by photoactivating materials mixed with the fluids. The systems and methods quantify the photoreactions that occur in a manner that permits correlation with clinical results.

4 Claims, 5 Drawing Sheets

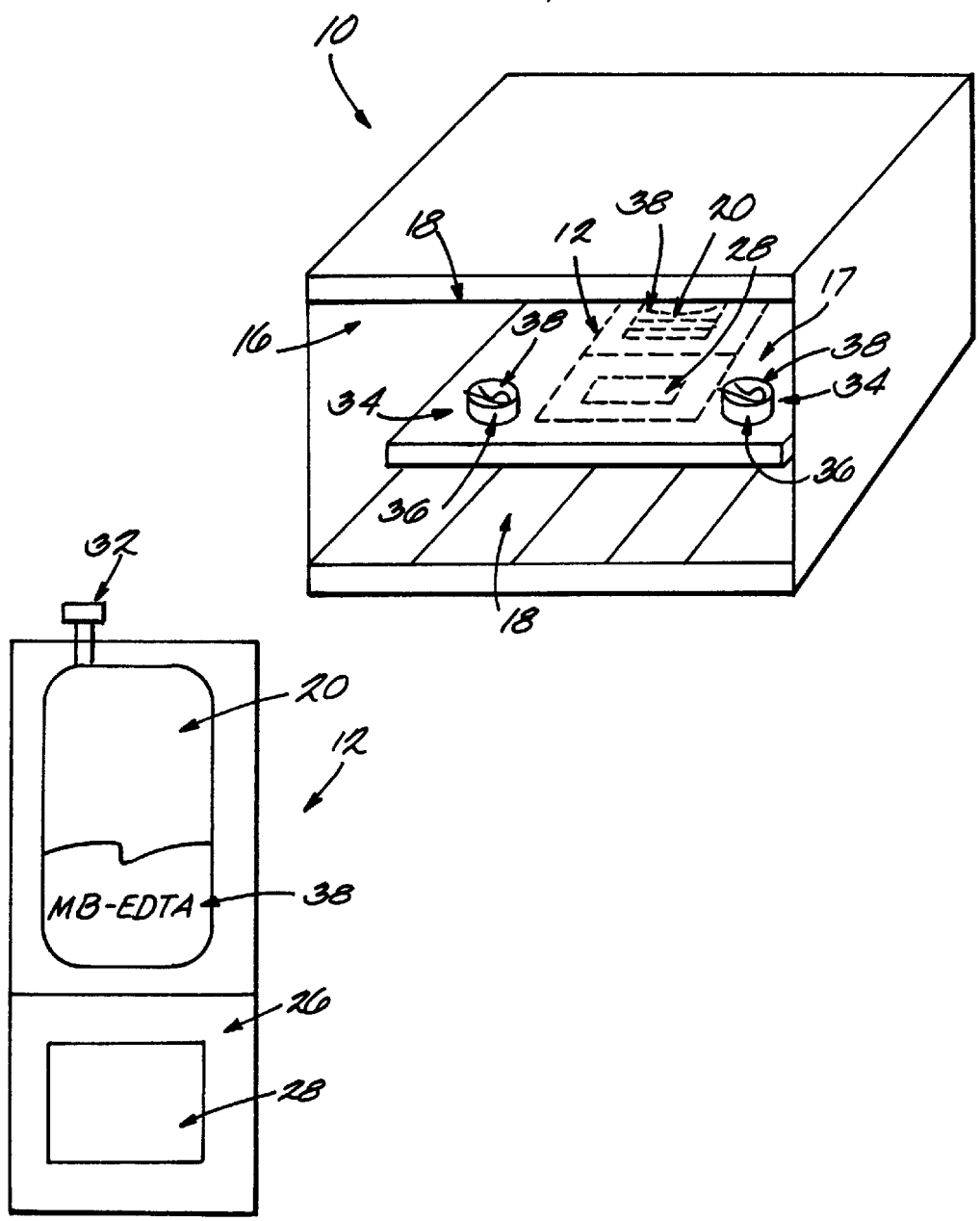

METHODS FOR QUANTIFYING PHOTOREACTIONS IN LIGHT ACTIVATED MATERIALS

This is a divisional of application Ser. No. 08/771,206 filed on Dec. 20, 1996, now U.S. Pat. No. 5,866,094.

FIELD OF THE INVENTION

The invention generally relates to the eradication of contaminants using photodynamic therapy. In a more specific sense, the invention relates to the treatment of biological fluids with methylene blue photoactive materials to eradicate viruses and other pathogenic contaminants.

BACKGROUND OF THE INVENTION

A biological fluid like human blood includes both cellular and noncellular components. The cellular components in blood include red blood cells (RBC), white blood cells (WBC), and platelets. Plasma is a non-cellular component of blood and is the liquid medium in which the cellular components are suspended.

It is well known that viruses, such as hepatitis or HIV virus, may be resident within human blood. The viruses residing in blood may be "intracellular," i.e. contained within one of the cellular components of blood, such as white blood calls, or they may be "extracellular," i.e. freely existing in the plasma. For example, the hepatitis virus is primarily an extracellular virus, the cytomegalovirus (the virus responsible for herpes) is primarily an intracellular virus, and the HIV virus (the virus responsible for AIDS) is found both intracellularly and extracellularly.

The medical community has developed methods and apparatus to remove virus from the blood stream or otherwise inactivate the virus.

A more recent approach to viral inactivation is the treatment of blood or blood components with a photochemical agent and light. When activated by light of an appropriate wavelength, the photochemical agent either kills the virus directly or indirectly inhibits the ability of the virus to replicate and, thus, in either case "inactivates" the virus. As used herein, the term "inactivate" (and ' forms thereof) mean the actual destructive, eradication of a contaminant such as a virus, or a direct or indirect effect on the contaminant that inhibits its ability to replicate or otherwise to adversely affect a living recipient.

Several known photochemical agents have been used or disclosed for use in inactivating viruses in blood. One such agent is methylene blue. As presently understood, a methylene blue molecule that has been activated by light becomes a catalyst for secondary and tertiary reactions that inactivate virus. More specifically, activation of the photochemical agent such as methylene blue is believed to result in the production of singlet oxygen which enhances the secondary and tertiary reactions. A detailed discussion of methylene blue, its photophysics, and photodynamic action on proteins, nucleic acid, viruses and bacteria is set forth in Tuit et al., "Photochemical interactions of methylene blue and analogues with DNA and other biological substrates," J. Photochea, Photobiol.B. Biol., 21, (1993) which is incorporated by reference herein.

In the development of light sources to illuminate methylene blue solutions so as to achieve a virucidal affect, there are many variables which can influence the photochemical yield of methylene blue excitation. Major variables include the wavelength of the light, the distance of the light source to the methylene blue solution, the geometry of the container containing the methylene blue, and the intensity of the light. It has been found difficult to reduce these variables to a single quantitative number, which can be used for standardization of light sources for methylene blue photochemistry and quality control/validation purposes.

For this and other reasons, the promise of photodynamic therapy in treating the nation's banked blood supply has gone largely unfulfilled.

SUMMARY OF THE INVENTION

The invention provides systems and methods for quantifying photoreactions in light sensitive materials, like methylene blue, during a targeted illumination period or periods.

One embodiment of the invention provides a system, which comprises a vessel for holding a liquid content. The vessel has a region transparent to prescribed light energy. The liquid content includes a solution carried within the vessel. The solution comprises a photoactive material which undergoes reduction oxidation in response to exposure to the prescribed light energy. The liquid content also includes a reducing agent mixed with the photoactive material.

Another embodiment of the invention provides a method for analyzing photoreactions in a light activated material. The method provides a light activated material having an oxidized state, which exhibits a first color, and a reduced state, which exhibits a second color different than the first color. The method provides a reducing agent to capture the photoactive material in the reduced state. The method mixes the reducing agent with the light activated material to form a mixture. The method obtains a first optical density measurement of the mixture without exposing the mixture to activating light energy. The method exposes the mixture to activating light energy, and obtains a second optical density measurement after the exposing step. The method compares the first and second optical density measurements.

The presence of the reducing agent mixed with the photoactive material enables a differential analysis of the optical density of the mixture before and after exposure to the prescribed light energy. The differential analysis quantifies the magnitude of photoreactions occurring as a result of the exposure to the prescribed light energy.

In a preferred embodiment, the photoactive material includes a phenothiazine dye, such as methylene blue. In this embodiment, the reducing agent includes ethylene-diamene-tetraacetic acid (EDTA).

Other features and advantages of the invention will be pointed out in, or will be apparent from, the drawings, specification and claims that follow.

DESCRIPTION OF THE DRAWINGS

FIG. 7 shows another embodiment the component which quantitatively measures the performance of the light chamber in terms of the amount of photoreactions that occur during a targeted dose period.

Figure 1:
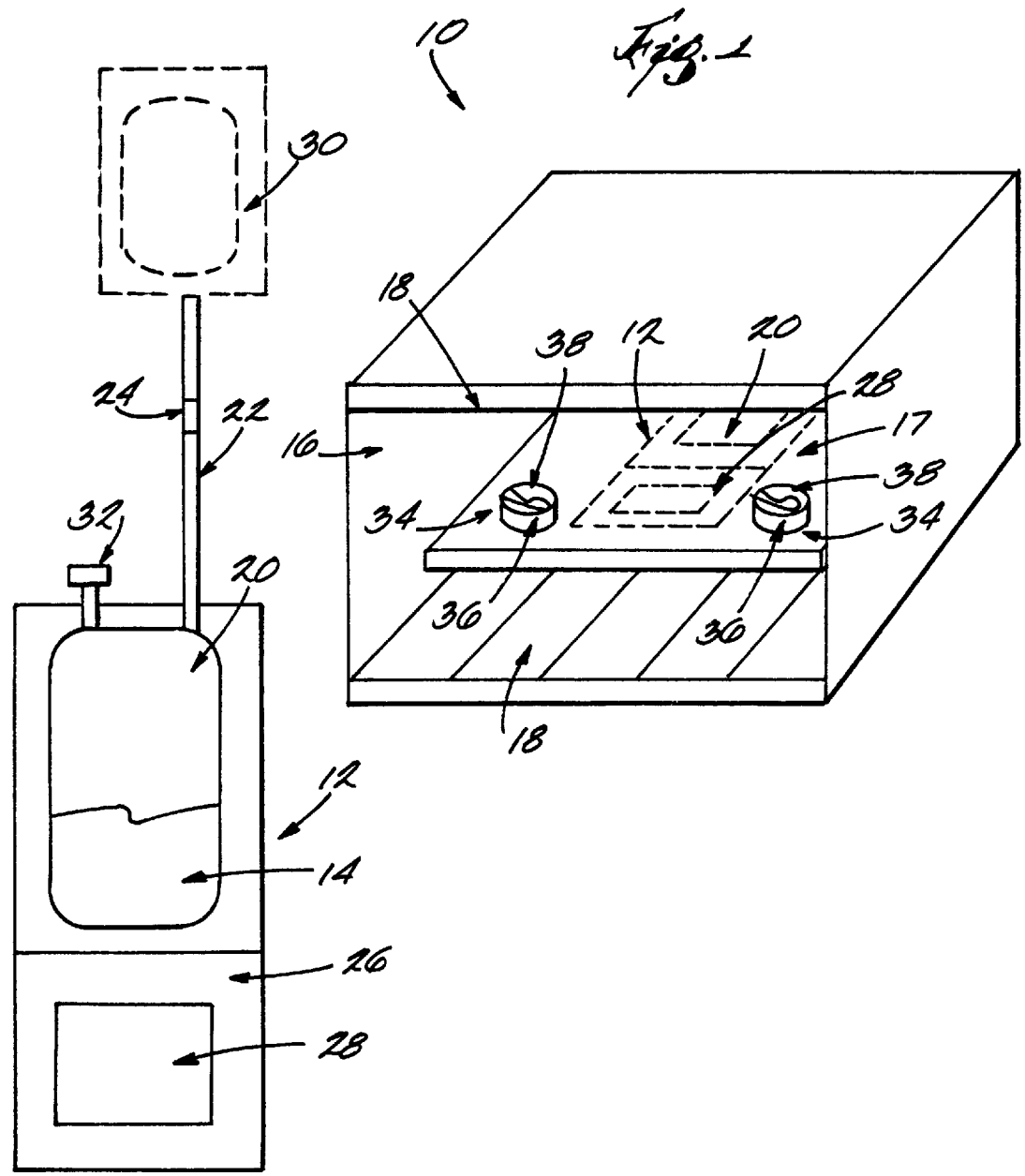
FIG. 1 is a view, partially plan and partially perspective, of a system for reducing the presence of viral agents in plasma, which includes a collection container and a light chamber.

The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

FIG. 1 shows a system 10, which is intended, during use, to assist in the removal of viral agents from plasma. The system 10 shown in FIG. 1 will be described in the context of reducing the presence of viral agents in single donor units of plasma, because it is particularly well suited for this purpose.

The system includes a processing and storage container 12, which contains a photoactive material 14. In use, plasma is conveyed into the container 14, where it is mixed with the photoactive material 14.

The system 10 also includes a light chamber 16. The container 12 holding the mixture of plasma and photoactive material 14 is placed on a tray 17 in the light chamber 16. The light chamber 16 includes light sources 18, which radiate light energy within a selected wavelength range from above and below the tray 17. The tray 17 is made of a light transmissive material (e.g., quartz), so that light from the sources 18 enters the plasma-photoactive material mixture in the container 12 lying on the tray 17. The light energy activates the photoactive material 14 and thereby eradicates free viral agents in the plasma.

In the illustrated embodiment, methylene blue, a thiazine dye, serves as the photoactive material 14. Methylene blue possesses the ability to bind to nucleic acids with high affinity, targeting the viruses for destruction upon exposure to a particular spectrum of light energy. Methylene blue absorbs light in the 660 nm region of the visible spectrum, which is the spectrum region where plasma is most transparent. Methylene blue inactivates a broad range of viruses, such as HIV, human hepatitis B (HBV), human hepatitis C (HCV), and Parvo virus B19, with minimal loss of therapeutic plasma proteins.

In a representative implementation, the container 12 is capable of holding between 235 to 310 mL of plasma, and the photoactive material 14 comprises about 10 mL of liquid solution containing 83 micrograms of methylene blue in water at pH 3.1, without buffers or other additives.

The processing and storage container 12 can be constructed in various ways. In the illustrated and preferred embodiment, the container 12 includes an interior chamber 20. Integrally attached transfer tubing 22 communicates with the chamber 20 for conveying plasma into the chamber 20. A conventional in-line cannula 24 is present in the tubing 22 to normally block fluid flow through it.

The container 12 is made of a material that is substantially transparent to the applied light energy. The material for the container 12 is also adapted to withstand contemplated storage conditions for the plasma (typically at temperatures below −30° C.). In the illustrated and preferred embodiment, the applied light energy is in the white light spectrum (400 to 700 nm). The container 12 is therefore made of a plastic, poly(ethylene vinyl acetate) material. This material is commercially available and is made and sold, for example, by Baxter Healthcare Corporation under the trademark PL-732® Plastic.

The container 12 also includes a flap 26, which extends below the chamber 20. The flap 26 carries a printed label 28 having identifying indicia. The flap 26 keeps the label 28 away from the chamber 20, where it could block or impede the irradiating light.

In the illustrated embodiment, the transfer tubing 22 is made from medical grade plasticized polyvinyl chloride plastic. However, other flexible medical grade plastic materials can be used.

In use, the transfer tubing 22 is connected in a sterile fashion to a source container 30 holding plasma (shown in phantom lines in FIG. 1). The source container 30 can, for example, hold fresh plasma or plasma that has been frozen and thawed. The plasma is harvested by conventional blood banking procedures.

Known sterile connection mechanisms (not shown) like that shown in Spencer U.S. Pat. No. 4,412,835 can be used for connecting the container 38 to the transfer tubing 22. These mechanisms form a molten seal between tubing ends, which, once cooled, forms a sterile weld.

Once the sterile connection is made, the source container 30 is suspended above the processing and storage container 12 (as FIG. 1 shows). The technician breaks the cannula 22, and the plasma flows by gravity head pressure into the processing and storage container 12.

While not shown in FIG. 1, the transfer tubing 22 can include an integrally attached, in-line filter that removes from plasma cellular matter, e.g., leukocytes, which does actually or potentially entrain viral agents.

A normally sealed outlet port 32 also communicates with the chamber 20. The port 32 is opened when it is time to remove plasma from the chamber 20.

The photoactive material 14 is mixed with the plasma within the chamber 20 by manual inversion. After air venting, the tubing 22 next to the container 20 is sealed closed using, for example, a dielectric tube sealer.

Further details of container 12 and its handling are found in copending U.S. patent application Ser. No. 08/121,820, filed Sep. 15, 1993, and entitled "Container for Irradiation of Blood Products" and copending U.S. patent application Ser. No. 08/742,572, filed Oct. 28, 1996, and entitled "Systems and Methods for Removing Viral Agents from Blood."

The light sources 18 comprise arrays of fluorescent lamps, which supply output in the visible range (400 to 700 nm) to both sides of the container 12. Representative lamps than can be used for this purpose are General Electric SPX35 white fluorescent light bulbs. The light chamber 16 monitors the light intensity and adjusts exposure time to control total light dosage delivered to the container 12. The approximate time of illumination to deliver a targeted dose of 33 J per cm$^3$ is 30 minutes. Further details of the light chamber can be found in U.S. Pat. Nos. 5,290,221 and 5,300,019.

After the illumination step, the plasma is frozen within the container 12 using conventional blood bank practices. The plasma within the container 12 is thawed when fractionation or transfusion is required.

As FIG. 1 shows, the system 10 includes a component 34, which quantitatively measures the performance of the light chamber 16 or the container 12, in terms of the amount of methylene blue photoreactions that occur during the targeted dose period.

Figure 2:
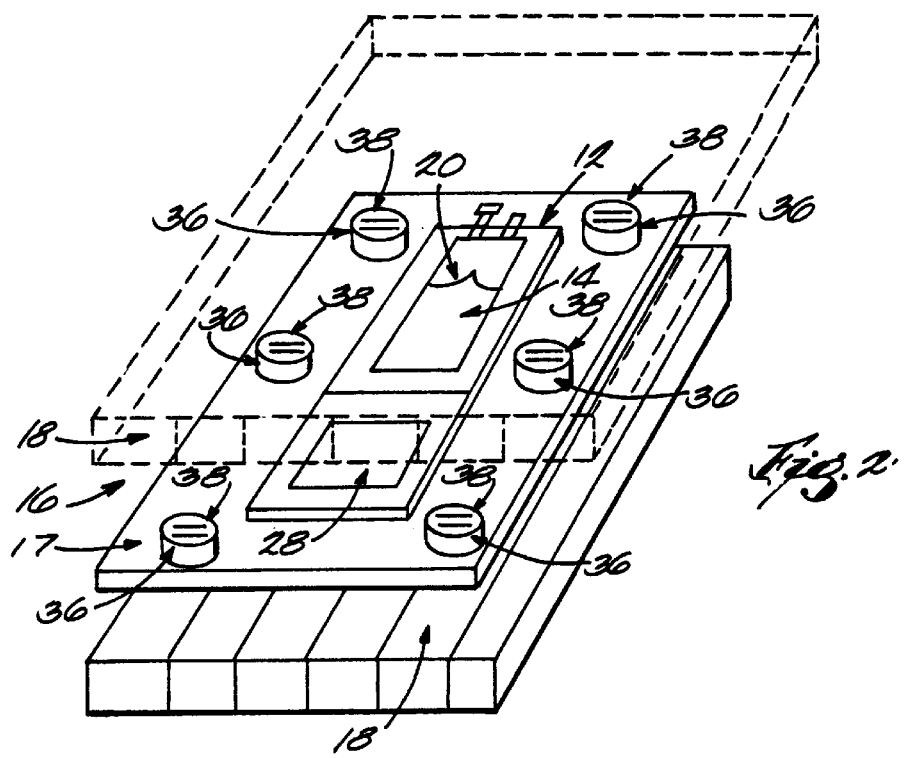
FIG. 2 is a perspective, largely diagrammatic view of the interior of the light chamber shown in FIG. 1, showing one embodiment the component which quantitatively measures the performance of the light chamber in terms of the amount of photoreactions that occur during a targeted dose period.

In the illustrated embodiment (see FIG. 2), the component 34 includes at least one, and preferably several, monitor dishes 36 carried by the tray 17 in the radiation path of light energy applied to the container 12. Each monitor dish 36 is made of a material that is transparent to the light energy applied by the light chamber to photoactivate the methylene blue (i.e., in the white light spectrum from 400 to 700 nm).

The component 34 further includes a prescribed solution 38 of methylene blue (MB) and the crystalline acid ethylene-diamene-tetraacetic acid ($C_{10}H_{16}N_2O_8$) (EDTA), which is present in each monitor dish 36. This solution 38 will be called the MB-EDTA solution.

Figure 3:
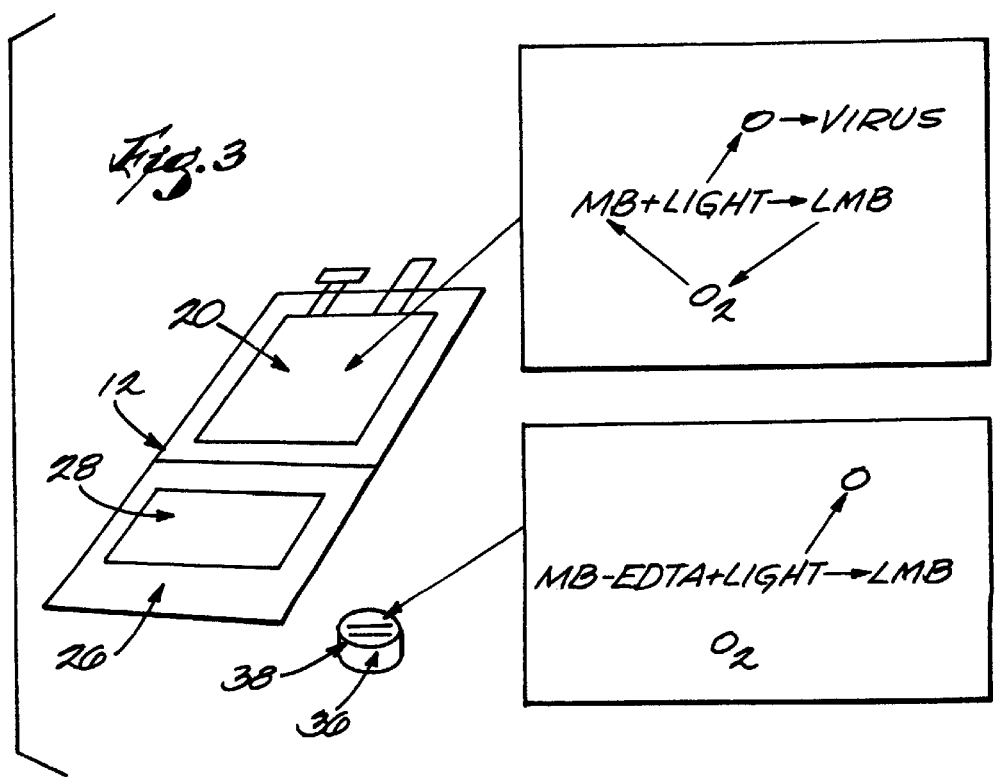
FIG. 3 is a perspective view, largely diagrammatic, schematically showing the photoreactions that occur in the performance-measuring component and the container when within the light chamber shown in FIG. 1.

As FIG. 3 shows, light within the light chamber 16 activates the methylene blue (MB) in both the container 12 and the monitor dish 36 to release singlet oxygen (O). Singlet oxygen (O) is the agent that inactivates viruses in the plasma within the container 12.

This photo-oxidation reaction occurs simultaneously in both the container 12 and the monitor dish 36 while light is being applied in the light chamber 16. In both the container 12 and the monitor dish 36, the reaction reduces methylene blue (MB) to leucomethylene blue (LMB). Leucomethylene blue (LMB) is a colorless compound, which does not absorb the radiated light and which is not effective in inactivating viruses.

In the presence of oxygen ($O_2$), which is present in the container 12, leucomethylene blue (LMB) will typically spontaneously revert back to methylene blue (MB), which is then capable of undergoing another photo-oxidation reaction. This chemical process is known as a reduction-oxidation reaction, wherein a compound (like MB) possesses a colored state when in an oxidized condition and a colorless state (like LMB) when in a reduced condition. However, the presence of EDTA in the monitor dish 36 blocks the conversion of leucomethylene blue (LMB) back to methylene blue (MB), despite the presence of oxygen ($O_2$) in the light chamber 16. In this respect, LMB can be characterized as a chemical reducing agent, which captures the reduced, colorless condition.

It has been discovered that the EDTA in the MB-EDTA solution 38 has no effect upon the absorbance by methylene blue (MB) of activating light energy, and no effect upon the photoreaction of methylene blue (MB) to leucomethylene blue (LMB). Both occur in essentially the same way in the container 12 and the monitor dish 36, whether or not EDTA is present.

The regeneration of leucomethylene blue (LMB) into methylene blue (MB) due to oxygen ($O_2$) in the container 12 tends to mediate measurable loss of absorbance (i.e., optical density) during a given irradiation cycle. However, the absorbance of irradiated light energy by the MB-EDTA solution 38 in the monitor dish 36 will diminish during the irradiation cycle in proportion to the number of methylene blue photoreactions that occur, because the LMB-to-MB-regeneration step is blocked by the EDTA. Thus, as the amount of methylene blue (MB) in the MB-EDTA solution 38 is reduced by photoreaction into colorless leucomethylene blue, absorbance of the irradiation energy by the remaining methylene blue MB in the solution 38 decreases. The loss of absorbance (i.e., the difference in optical density at a selected wavelength before illumination and after illumination) by the solution 38 within the monitor dish 36 quantitatively correlates with methylene blue photoactivation.

Figure 4:
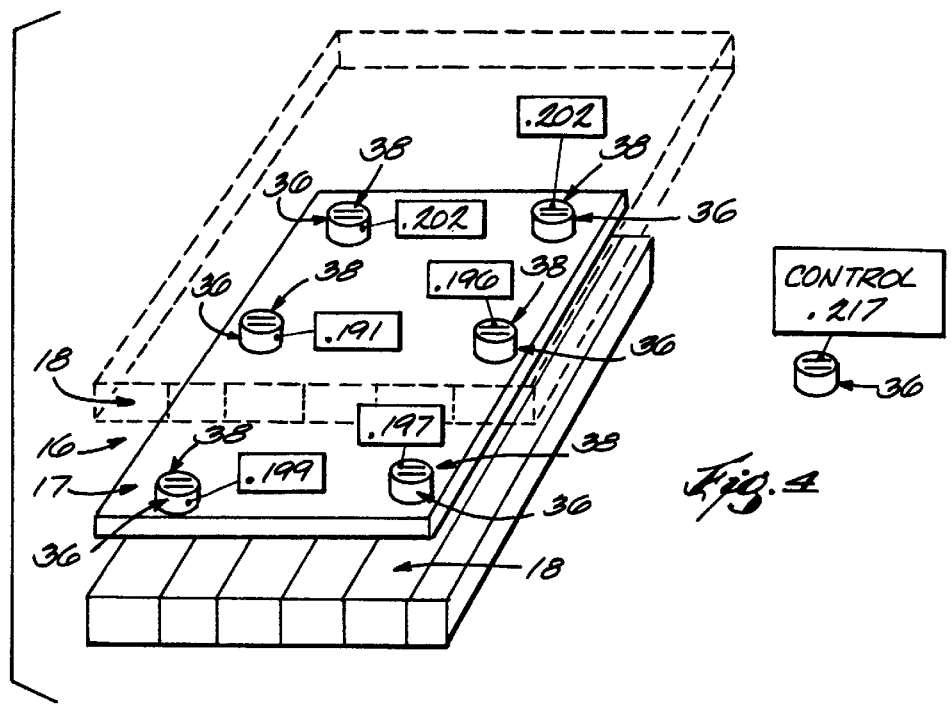
FIG. 4 is a perspective, largely diagrammatic view of the interior of the light chamber shown in FIG. 1, showing another embodiment the component which quantitatively measures the performance of the light chamber in terms of the amount of photoreactions that occur during a targeted dose period.

As FIG. 4 shows, placing monitor dishes 36 containing MB-EDTA solution 38 at different spatial locations on the tray 17 within the light chamber 16 makes it possible to monitor the pattern of irradiation within the chamber during a given photoactivation cycle, with or without the container 12 being present. Localized regions of lower irradiation exposure present within the chamber 16 can be quantitatively detected and corrected.

EXAMPLE 1

40 ml of methylene blue (MB) stock solution [MB 207 mg/L (anhydrous weight, MW=320) at pH 3.0] was diluted in a 1 L volumetric flask with distilled water at pH 3.0, to produce a 25 $\mu$M MB working solution. The working solution was protected from ambient light.

A stock solution of disodium EDTA (MW=372.2) was prepared in distilled water at 465 mg/L (1.25 mM). 22 ml of the EDTA stock solution was diluted in a 1 L volumetric flask with distilled water to produce a 28 $\mu$M EDTA working solution.

A MB-EDTA solution 38 was made by adding 50 ml MB working solution to a 500 ml volumetric flask with the EDTA working solution. The MB-EDTA solution 38 was protected from ambient light prior to use.

10 ml of the MB/EDTA solution 38 was added to seven monitor dishes 36, each of which comprised a 50 mm glass petri dish, with no surface charge and with no lid. Six of the monitor dishes 36 were placed at spaced apart positions on the tray 17 within a light chamber 16 (as FIG. 4 shows), and were illuminated for one duty cycle. The remaining monitor dish 36 was reserved as a control outside the light chamber and protected from light.

Absorbance of the MB-EDTA solution 38 at 663 nm was measured in each monitor dish 36, using the EDTA working solution to blank the spectrophotometer. The spectrophotometer can, for example, be a Perkin Elmer Lamba 3B UV/VIS, adjusted to read an absorbance at a wavelength of 633 nm and blanked according to the manufacturer's instructions manual. The absorbance measurement is taken using conventional 1 mL quartz cuvettes having a light path of 1 cm.

FIG. 4 shows in boxes the absorbance values of the MB-EDTA solution 38 in the monitor dishes 36 illuminated within the light chamber 16, as well as the absorbance value of the MB-EDTA solution in the control monitor dish 36.

The uniformly lower absorbance values of the MB-EDTA solution 38 in the monitor dishes 36 within the light chamber 16, compared to the control value, is quantitatively indicative of the magnitude of methylene blue photoreduction that occurred within the light chamber 16 during the duty cycle. The spatial variation of the absorbance values within the light chamber 16 (which FIG. 4 shows) also indicates the variation of the illumination pattern within the light chamber.

Figure 5:
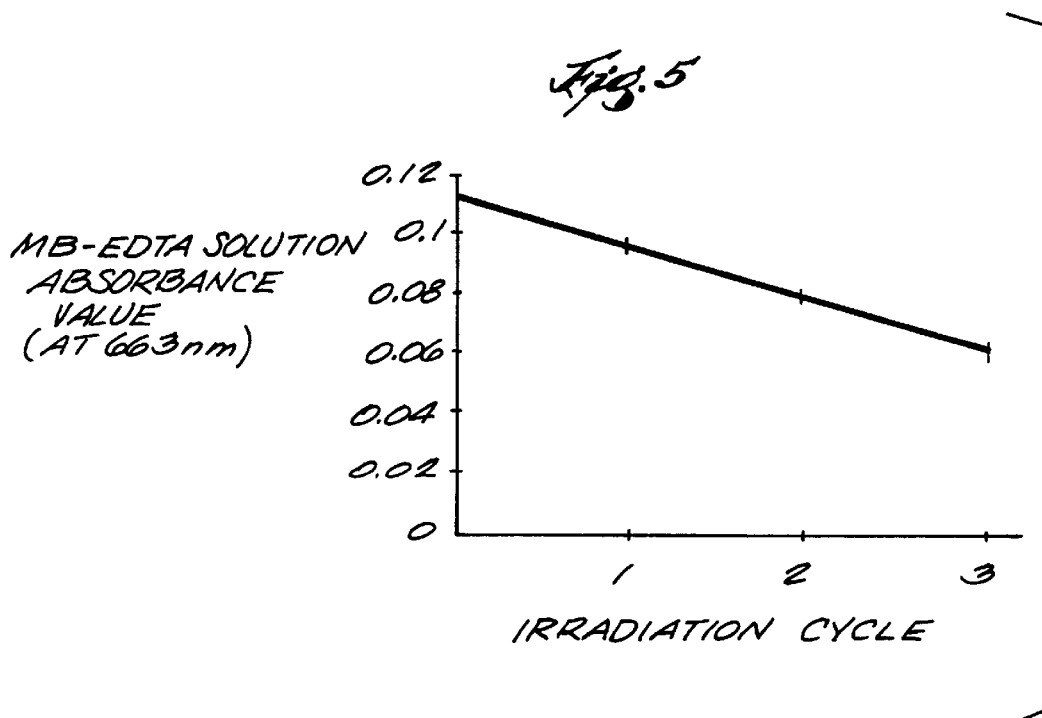
FIG. 5 is a graph showing the relationship between light absorbance measured by the component in relation to successive light illumination cycles.

FIG. 5 shows a representative plot of absorbance values (Y-axis) versus illumination cycles (X-axis). The plot demonstrates a good linear fit (y=−0.017x+0.111, $r^2$=0.999) between reduction of absorbance values (i.e., EDTA catalyzed photoreduction of methylene blue) during three successive illumination cycles.

Use of the MB-EDTA solution 38 in the monitor dishes 36 as just described also makes it possible to detect variations in irradiation from one photoactivation cycle to the next in an individual light chamber 16. Degradation of performance can therefore be identified for correction.

The MB-EDTA solution 38 in the monitor dishes 36 can also be used to compare different light chambers, to thereby quantitatively evaluate and compare photochemical effects upon methylene blue.

As FIG. 1 shows, one or more monitor dishes 36 with MB/EDTA solution 38 can be placed on the tray 17 in the light chamber 16 at the same time a containers 12 with plasma mixed with methylene blue is irradiated. In this way, clinical data derived from analyzing viral agent reduction in irradiated plasma present within the container 12 can be correlated with the absorbance values obtained from the MB-EDTA solution 38 in the monitor dishes 38 present in the light chamber 16 during the same irradiation cycle. Statistical correlations between quantitative absorbance values with quantitative clinical can be obtained, and quality control and monitoring criteria can be developed based upon quantitative absorbance values.

Figure 6:
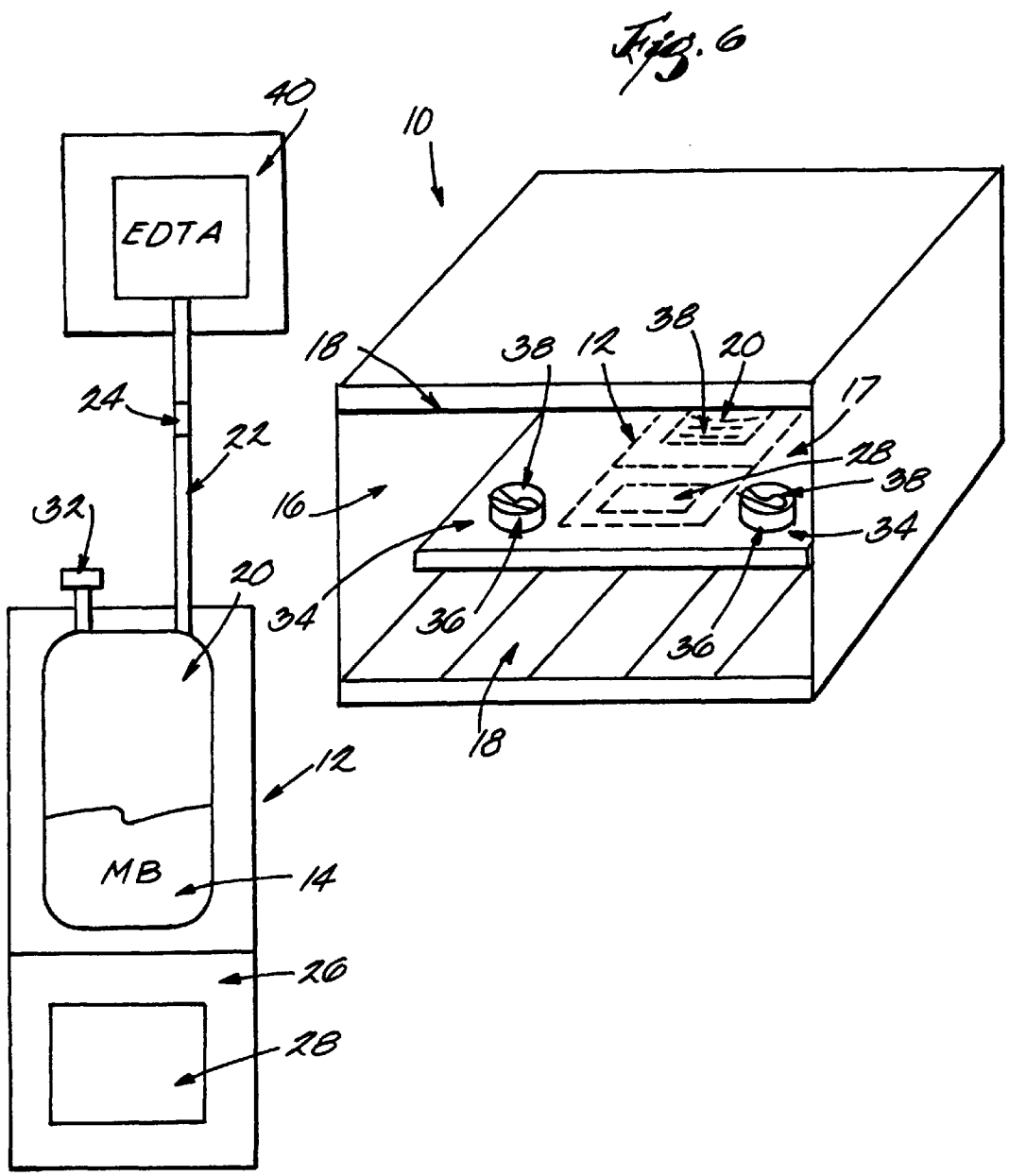
FIG. 6 shows another embodiment the component which quantitatively measures the performance of the light chamber in terms of the amount of photoreactions that occur during a targeted dose period.

In another embodiment (see FIG. 6), EDTA solution 40 is mixed with methylene blue 14 within the container 12, with no plasma present, forming the MB-EDTA solution 38. Alternatively (see FIG. 7), a test container 12 can be supplied by the manufacturer holding a premixed quantity of MB-EDTA solution 38. By measuring an absorbance value of the MB-EDTA solution 38 before and after illumination within the container 12 inside the light chamber 16 (with no plasma present) (as FIGS. 6 and 7 show), an illumination characteristic for the container 12 itself can be ascertained. By irradiated both the container 12 (with MB-EDTA solution 38) and one or more monitor dishes 36 (holding the MB-EDTA solution 38) at the same time within the light chamber 16, the illumination characteristics of both the container 12 and the light chamber 16 can be ascertained, making possible an evaluation of the system 10 as a whole. The evaluation is superior to using a conventional light meter, because it takes into account the variable absorption of different wavelengths of light by MB and the effects of geometry of the container 12

EXAMPLE 2

A MB-EDTA solution 38 was prepared and placed into containers 12 normally used to contain plasma in the presence of MB for illumination.

The MB-EDTA Solution was prepared as follows:

1. Measure out 4±0.01 L of high purity water into a 6 L erlenmeyer flask. Add 36.28±0.01 g of potassium phosphate-monobasic. Place a magnetic stir bar into the flask and spin until all the potassium phosphate has dissolved. Store this solution at room temperature in a carboy and designate as "Solution A."

2. Measure out 4±0.01 L of high purity water into a 6 L erlenmeyer flask. Add 37.86±0.01 g of potassium phosphate-dibasic. Place a magnetic stir bar into the flask and spin until all the potassium phosphate has dissolved. Store this solution at room temperature in a carboy and designate as "Solution B."

3. Measure out 826±1 mL of Solution A and 1174±1 mL of Solution B into a 20 L carboy covered in aluminum foil.

4. Dissolve 0.512±0.001 g of EDTA disodium salt, dihydrate into a 1000 mL volumetric flask with high purity water.

5. Add 40±1 mL of EDTA solution (Step 4) into the 20 L carboy containing Solution A and Solution B (Step 3).

6. Add 2 mL of 1 N HCl to 2000±10 mL of high purity water. Designate this solution as "Acidified Water."

7. Add 255±1 mg of MB (trihydrate) to 1000 mL of Acidified Water (Step 6). Mix well. Designate this solution as "MB Stock Solution." This solution is light sensitive and is stored at room temperature in a storage container covered in aluminum foil.

8. Dilute 40±1 mL of MB Stock Solution (Step 7) in a 1000 mL volumetric flask with Acidified Water (Step 6). Designate this solution as "MB Diluted Solution." This solution is also light sensitive and is stored at room temperature in a storage container covered in aluminum foil.

9. Add 200±1 mL of MB Diluted Solution (Step 8) to the 20 L carboy containing Solution A, Solution B, and EDTA (Step 5). This solution is mixed thoroughly using a magnetic stir bar. Designate this solution as "MB-EDTA Solution." This solution is light sensitive and is stored at room temperature in a storage container covered in aluminum foil.

10. Repeat steps 1 to 9 eight times to obtain a total volume of approximately 18 (17.92) L of MB-EDTA Solution.

A 15 mL sample was removed from the 20 L carboy containing the MB-EDTA Solution for analysis on the spectrophotometer and pH meter. The criteria was to assure that the MB-EDTA solution possessed a absorbance measurement (at 663 nm) greater than 0.19 and less than or equal to 0.23, and a pH measurement of 6.7±0.1. The spectrophotometer used was a Perkin Elmer Lamba 3B UV/VIS, adjusted to read an absorbance at a wavelength of 663 nm. The instrument was blanked according to the manufacturer's instructions manual using distilled water as the blanking solution. Absorbance measurements were taken in 1 mL quartz cuvettes having a light path of 1 cm.

The MB-EDTA Solution was stored at room temperature in a dark location.

Approximately 2000 mL of the MB-EDTA Solution was transferred to a 3000 mL Viaflex® Container (Baxter Healthcare Corporation, Deerfield, Ill.), which was wrapped completely in aluminum foil. Using a Terumo® SCD 312 Sterile Connector Device (Terumo, Japan), an empty illumination container in the form shown in FIG. 1 made from PL-732® Plastic Material (Baxter Healthcare Corporation, Deerfield, Ill.) was sterile connected to the Viaflex® Container holding the MB-EDTA Solution. The illumination container was placed onto an analytical balance, and the balance was tared. 270±2 g of MB-EDTA Solution was allowed to enter the illumination container. Once filled, the illumination container was sealed using a SEBRA™ hand sealer. Fourteen illumination containers were filled with MB-EDTA Solution in this way and stored at 22°±2 C. These containers were identified 1A, 1B, 2A, 2B, 3A, 3B, 4A, 4B, 5A, 5B, 6A, 6B, 7A, and 7B. During storage, the illumination containers were shielded from exposure to light.

Each illumination container was subject to end over end inversion at least three times to well mix the MB-EDTA Solution within it. A 5 mL syringe fitted with an 18 gauge needle withdrew a 3 mL sample of MB-EDTA Solution from each bag (through a conventional injection site coupler integrally attached to the container during manufacture). The port area of each container was first flushed with MB-EDTA solution by withdrawing and then injecting the solution prior to withdrawal of the sample. Each sample was immediately subjected to spectrophotometric analysis. The absorbance was measured at 633 nm using the spectrophotometer (Perkin Elmer Lambda 3b UV/VIS), which had been blanked with water according to manufacturer's instructions. A single quartz cuvette with a standard 1 cm optical pathlength was used. The cuvette was emptied and rinsed at least one time with the MB-EDTA Solution to be measured prior to taking an absorbance measurement. The absorbance value was entered as the initial absorptivity for the MB-EDTA Solution in each container.

Illumination containers 1A/1B, 2A/2B, and 3A/3B were placed inside a light chamber of a Baxter Illuminex™ 2000 Light Source (Baxter Healthcare Corporation, Deerfield, Ill.), which supplies an intense singular wavelength of red light energy. The exposure time varied between 627 seconds to 752 seconds (see Table 1 below). 3 mL samples were removed by syringe from each illumination container immediately after illumination in the manner described above. The samples were subjected to spectrophotometric analysis in the manner above described. The absorbance value was entere, as the final absorptivity for the MB-EDTA Solution in each container.

The measured difference in absorptivity was calculated by subtracting the final absorptivity from the initial absorptivity.

The following Table 1 summarizes the results.

TABLE 1

| Exposure Time (Sec) | 627 | 690 | 752 |
|---|---|---|---|
| Container # | 1A | 2A | 3A |
| Initial Absorptivity | 0.202 | 0.200 | 0.197 |
| Final Absorptivity | 0.094 | 0.085 | 0.080 |
| Change in Absorptivity | 0.108 | 0.115 | 0.117 |
| Exposure Time (Sec) | 627 | 690 | 752 |
| Container # | 1B | 2B | 3B |
| Initial Absorptivity | 0.201 | 0.197 | 0.215 |
| Final Absorptivity | 0.093 | 0.084 | 0.092 |
| Change in Absorptivity | 0.108 | 0.113 | 0.123 |
| Average Change in Absorptivity | 0.108 | 0.114 | 0.120 |

The above procedure was repeated for illumination containers 4A/4B, 5A/5B, 6A/6B, and 7A/7B using different white light fluorescent light devices (D1 to D4). Each device took the form generally shown in FIG. 1, equipped with General Electric SPX35 white fluorescent light bulbs. The devices were programmed to deliver 33 $J/cm^2$ of light energy (±10%). Final absorptivity values were obtained after each illumination.

The measured difference in absorptivity was calculated by subtracting the final absorptivity from the initial absorptivity.

The following Table 2 summarizes the results.

TABLE 2

| Device/Programmed Energy ($J/cm^2$) | D1/33 | D2/33 | D3/33 | D4/33 |
|---|---|---|---|---|
| Container # | 4A | 5A | 6A | 7A |
| Initial Absorptivity | 0.205 | 0.206 | 0.205 | 0.206 |
| Final Absorptivity | 0.080 | 0.093 | 0.087 | 0.090 |
| Change in Absorptivity | 0.125 | 0.113 | 0.118 | 0.116 |
| Programmed Energy ($J/cm^2$) | 33 | 33 | 33 | 33 |
| Container # | 4B | 5B | 6B | 7B |
| Initial Absorptivity | 0.203 | 0.202 | 0.203 | 0.201 |
| Final Absorptivity | 0.079 | 0.090 | 0.082 | 0.084 |
| Change in Absorptivity | 0.124 | 0.112 | 0.121 | 0.117 |
| Average Change in Absorptivity | 0.125 | 0.113 | 0.120 | 0.117 |

Example 2 demonstrates that the MB-EDTA Solution can be used to detect small variations in illumination dosage. Example 2 demonstrates that the MB-EDTA Solution can effectively verify light treatment dosages.

The embodiments show the invention used, for the purpose of illustration, in association with a system that uses methylene blue as the photoactive material and EDTA as the reducing agent. However, it should be appreciated that the invention has broader applicability, and can be used with systems that use any photoactive material that undergoes a reduction oxidation reaction, whether for viral inactivation or for another purpose. Reduction oxidation materials are characterized by exhibiting a known colored state when in an oxidized condition and a known colorless state when in a reduced condition. Reducing agents can be selected for such materials, to capture the material in its reduced condition for spectrophotometric analysis. For example, all phenothiazine dies, such as methylene blue, Azure B, Azure A, Azure C, and thionine, possess a known color oxidant (blue, except for thionine, which is violet) and a known colorless reduction. Phenol blue, nile blue, and o-Tolidine also exhibit a known color oxidant (blue) and a known colorless reduction. Reducing agents like EDTA, scorbic acid, allylthiourea (ATU), and ferrous sulfate can be selected to capture such materials in the reduced state for spectrophotometric analysis at a selected effective wavelength according to the invention. The wavelength selected for spectrophotometric analysis need not be 663 nm (as shown in the illustrated embodiments), but can also vary from about 550 nm to about 690 nm. Fluorescein dyes are yet another example of a class of material that undergoes reduction oxidation, which can be captured using a reducing agent, such as ATU, for spectrophotometric analysis at a selected effective wavelength according to the invention. By way of another example, acridine dyes are yet another class of material that undergoes reduction oxidation, which can be captured using a reducing agent, such as a reducing amine, for spectrophotometric analysis at a selected effective wavelength according to the invention.

Features and advantages of the invention are set forth in the following claims.

We claim:

1. A method for analyzing photoreactions in a light activated material comprising the steps of providing a light activated material having an oxidized state, which exhibits a first color, and a reduced state, which exhibits a second color different than the first color, providing a reducing agent to capture the photoactive material in the reduced state, mixing the reducing agent with the light activated material to form a mixture, obtaining a first optical density measurement of the mixture without exposing the mixture to activating light energy, exposing the mixture to activating light energy, obtaining a second optical density measurement after the exposing step, and comparing the first and second optical density measurements.

2. A method according to claim 1 wherein the photoactive material includes a phenothiazine dye.

3. A method according to claim 2 wherein the phenothiazine dye includes methylene blue.

4. A method according to claim 3 wherein the reducing agent includes ethylene-diamene-tetraacetic acid.

* * * * *